United States Patent
Pfister et al.

(10) Patent No.: US 8,929,631 B2
(45) Date of Patent: Jan. 6, 2015

(54) METHOD AND DEVICE FOR AUTOMATICALLY ADAPTING A REFERENCE IMAGE

(75) Inventors: Marcus Pfister, Bubenreuth (DE); Martin Von Roden, Aurora, OH (US)

(73) Assignee: Siemens Aktiengesellschaft, Munich (DE)

( * ) Notice: Subject to any disclaimer, the term of this patent is extended or adjusted under 35 U.S.C. 154(b) by 803 days.

(21) Appl. No.: 13/053,623

(22) Filed: Mar. 22, 2011

(65) Prior Publication Data

US 2011/0235876 A1    Sep. 29, 2011

(30) Foreign Application Priority Data

Mar. 24, 2010    (DE) .................. 10 2010 012 621

(51) Int. Cl.
| | | |
|---|---|---|
| *G06K 9/00* | (2006.01) | |
| *G06K 9/32* | (2006.01) | |
| *A61B 5/05* | (2006.01) | |
| *A61B 6/00* | (2006.01) | |
| *G06T 7/00* | (2006.01) | |
| *A61B 19/00* | (2006.01) | |
| *A61F 2/82* | (2013.01) | |

(52) U.S. Cl.
CPC .............. *A61B 6/504* (2013.01); *A61B 6/5247* (2013.01); *G06T 7/0024* (2013.01); *A61B 6/487* (2013.01); *A61B 6/5211* (2013.01); *G06K 2209/057* (2013.01); *G06T 2207/30048* (2013.01); *G06T 2207/10121* (2013.01); *G06T 2207/30021* (2013.01); *G06T 2207/10081* (2013.01); *A61B 2019/5287* (2013.01); *A61B 2019/5265* (2013.01); *A61B 19/5244* (2013.01); *A61F 2/82* (2013.01)

USPC .......... 382/130; 382/131; 382/294; 600/424; 600/427

(58) Field of Classification Search
USPC ................ 382/100, 103, 128–132, 154, 285; 600/101, 117, 407–41, 420, 425–426, 600/431–435, 437–461
See application file for complete search history.

(56) References Cited

U.S. PATENT DOCUMENTS

| | | | |
|---|---|---|---|
| 6,351,513 B1 * | 2/2002 | Bani-Hashemi et al. | 378/8 |
| 6,501,848 B1 * | 12/2002 | Carroll et al. | 382/128 |
| 8,275,448 B2 * | 9/2012 | Camus et al. | 600/428 |
| 8,600,477 B2 * | 12/2013 | Beyar et al. | 600/424 |
| 2004/0066958 A1 * | 4/2004 | Chen et al. | 382/128 |
| 2005/0182295 A1 * | 8/2005 | Soper et al. | 600/117 |
| 2006/0023840 A1 * | 2/2006 | Boese | 378/98.12 |
| 2006/0241465 A1 * | 10/2006 | Huennekens et al. | 600/458 |
| 2007/0025605 A1 * | 2/2007 | Bohm et al. | 382/128 |
| 2008/0147086 A1 | 6/2008 | Pfister et al. | |
| 2009/0281452 A1 * | 11/2009 | Pfister et al. | 600/567 |
| 2010/0222671 A1 * | 9/2010 | Cohen et al. | 600/424 |
| 2011/0201915 A1 * | 8/2011 | Gogin et al. | 600/407 |

FOREIGN PATENT DOCUMENTS

| | | |
|---|---|---|
| DE | 10 2007 057 096 A1 | 5/2008 |
| DE | 10 2007 032 786 A1 | 1/2009 |
| DE | 10 2007 052 123 A1 | 5/2009 |

* cited by examiner

*Primary Examiner* — Randolph I Chu
*Assistant Examiner* — Nathan Bloom

(57) ABSTRACT

A method and a device for reference image adapting in the field of fluoroscopy-controlled interventional repair of abdominal aortic aneurisms on angiography systems are proposed. Displacements which can be brought about as a result of introducing instruments, such as when a stent is deployed in an aorta, are automatically corrected. It is also possible to correct such displacements which initially cannot be perceived in the image due to the angle of view.

13 Claims, 6 Drawing Sheets

FIG 2    Prior Art
a)
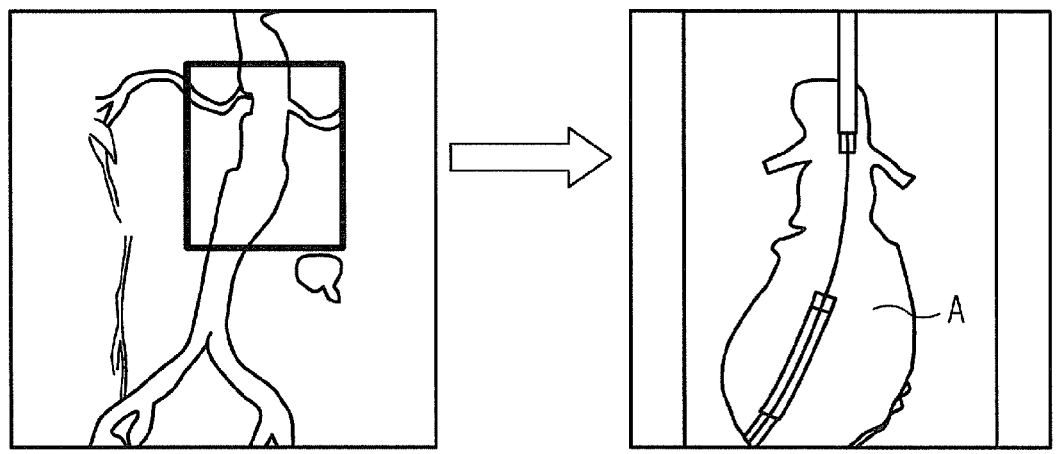
b)
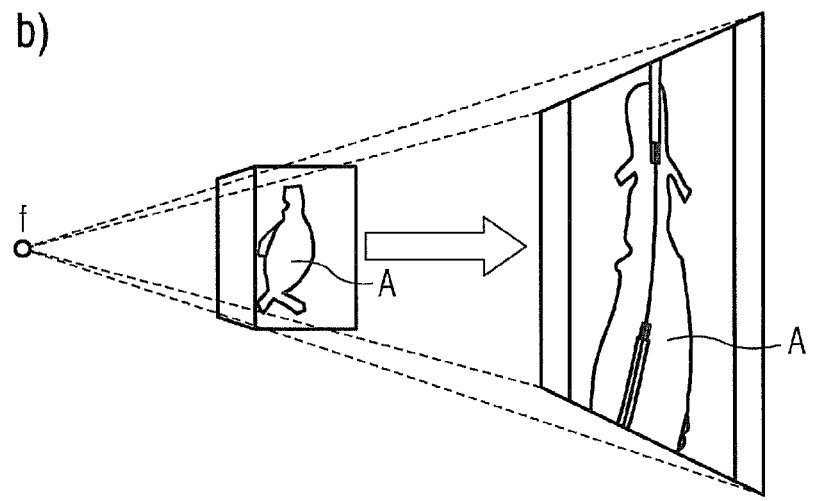

FIG 3    Prior Art
a)
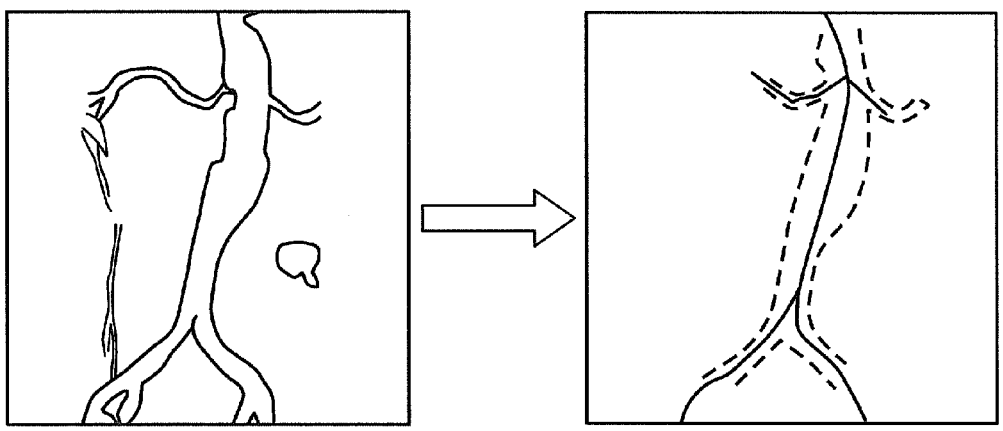
b)
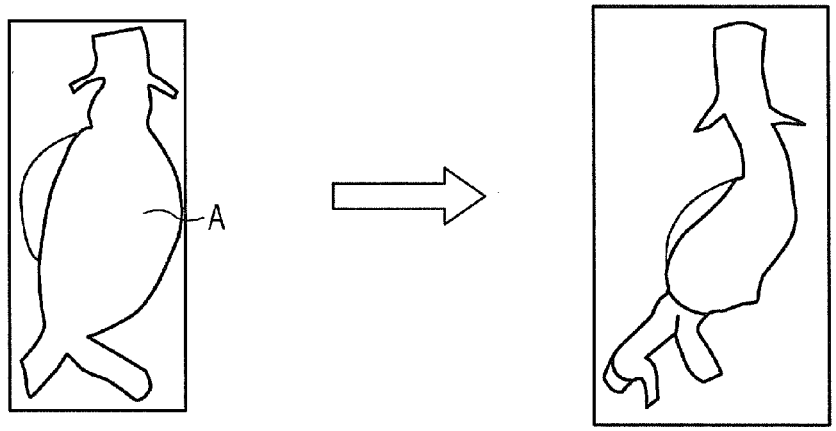

FIG 5
a)
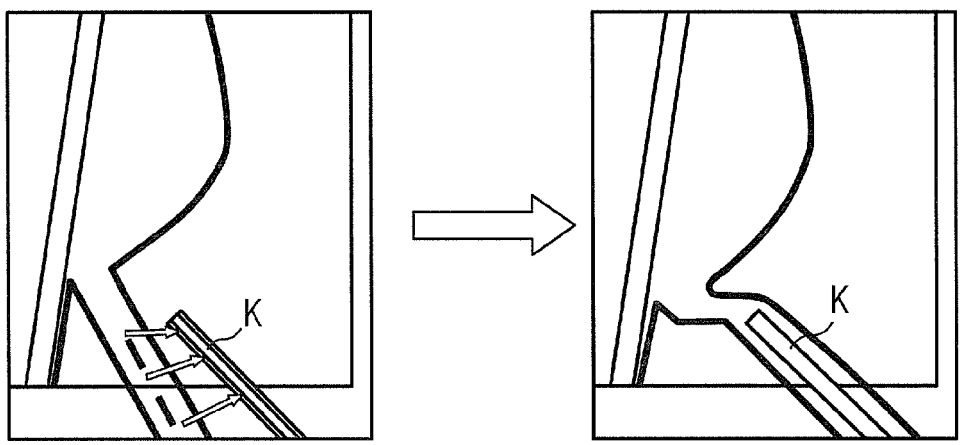
b)
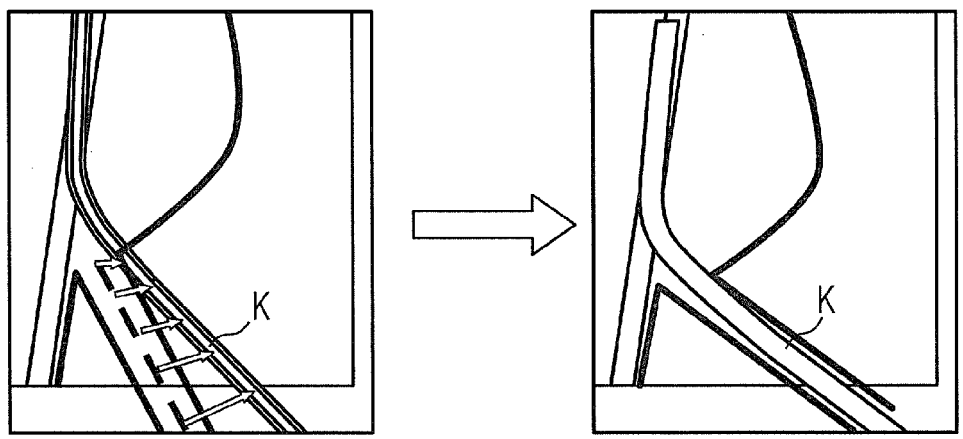

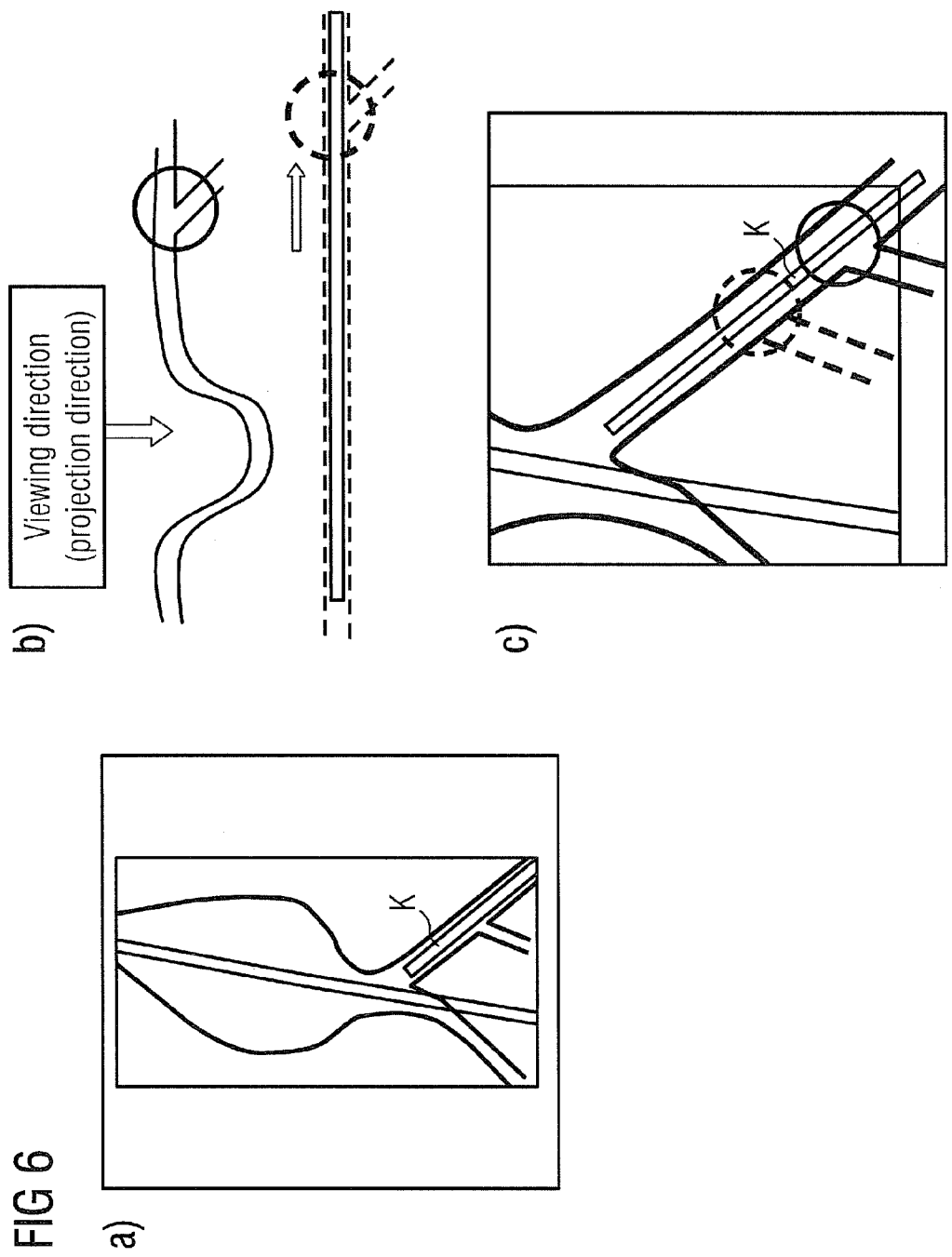

METHOD AND DEVICE FOR AUTOMATICALLY ADAPTING A REFERENCE IMAGE

CROSS REFERENCE TO RELATED APPLICATIONS

This application claims priority of German application No. 10 2010 012 621.7 filed Mar. 24, 2010, which is incorporated by reference herein in its entirety.

FIELD OF THE INVENTION

The invention relates to the field of fluoroscopy-controlled interventional repair of abdominal aortic aneurisms (=AAA) on angiography systems.

BACKGROUND OF THE INVENTION

An abdominal aortic aneurism is a dilatation of a vessel on the abdominal aorta. This condition is treated by insertion of a so-called stent graft, i.e. composite angioplasty devices. Guide wires and catheters are inserted into the aorta via both groins and one or more stent grafts are introduced via said guide wires and catheters. An abdominal aortic aneurism A of this type is shown by way of example in FIG. 1a. It is treated by insertion of a stent graft S. Guide wires and/or catheters K are inserted into the aorta via both groins and the stent grafts are introduced with the aid of said guide wires and catheters.

The aim when inserting said stent grafts is to place the "landing zone" of the vascular graft as far as possible in the healthy vessel wall region, though at the same time taking care that no important branch vessels are covered. In particular the branches of the renal arteries, of the superior mesenteric artery (arteria mesenterica superior), of the truncus coeliacus, and of the internal iliac arteries (a. iliaca interna) must be kept free. A sensitive point is the placement of the "main stent" in the aorta, in which case the cited branch vessels must not be occluded. In the case of complex stents which include the leg arteries, as shown for example in FIG. 1c, the final stent must sometimes be composed of "partial stents" (e.g. an aortic stent (I) to which the stent for the leg artery (II) is attached through what is termed a fenestration).

In order to avoid the necessity of injecting contrast agent to allow constant vessel visualization for monitoring purposes during the complex stent positioning procedure it is possible to overlay a reference image (anatomically correctly) in the manner of a positioning aid, which reference image renders the vessels (in this case aorta and branch vessels). As shown in FIG. 2a, said reference image can either be a 2D angiogram (DSA) or, as shown in FIG. 2b, it can beneficially be a previously recorded 3D dataset (e.g. a CT angiography sequence) of the aneurysm. These show more details and can be overlaid at any angulation of the C-arm.

As shown in FIG. 3, it is possible to pre-segment the aneurysm from the reference images. In this case the course of the vessel (centerline) or the contours of the vessels can be determined, for example. This can happen both in the case of the 2D reference image, as shown in FIG. 3a, and in the case of the 3D reference image, as shown in FIG. 3b. Furthermore it is possible to identify and track instruments (e.g. catheters or guidance devices) in 2D images. As already shown in FIG. 2, a partially flexible 2D-3D or 3D-3D registration, e.g. of 2D and 3D angiography images, is possible.

A problem with said overlays is that the reference image (2D or 3D) shows the vessel anatomy at a specific instant in time. If, as shown e.g. in FIG. 4, the physician introduces very inflexible or rigid instruments, e.g. a catheter K, the anatomy is deformed. If said deformation is not corrected in the overlaid reference image (see FIGS. 4a and 4b), an imprecision or a discrepancy arises when the reference image is superimposed. This can lead to uncertainties in navigation during an intervention in which the overlay serves as a navigation aid.

SUMMARY OF THE INVENTION

As mentioned in the introduction, it is the object of the invention to correct deformations of said kind.

The object is achieved by means of the method and the device as claimed in the independent claims. Advantageous embodiments of the method and of the device are the subject matter of the dependent claims or can be derived from the following description and the exemplary embodiments.

The subject matter of the invention is a method for adapting at least one reference image, suitable in particular for inserting a stent into an aorta, which automatically corrects displacements which can be brought about as a result of introducing instruments, e.g. a catheter. At the same time it is preferred if displacements of the kind which initially cannot be perceived or are not visible in the image at corresponding viewing angles can also be corrected.

A further aspect of the invention is a device for the above-described adapting method, the device having means for performing the said adaption. The embodiment variants characterized in the dependent claims in relation to a method according to the invention also apply in respect of the device according to the invention.

The invention thereby increases the precision in the overlaid reference image which serves as a navigation aid during a medical intervention.

BRIEF DESCRIPTION OF THE DRAWINGS

Further advantages, details and developments of the invention will emerge from the following description of exemplary embodiments in conjunction with the drawings, in which:

FIGS. 1, 2, 3 and 4 cited in the introduction show the possible prior art and the above-described problem of deformation, and FIGS. 5a and 5b show the correction according to the invention in the image plane, and FIGS. 6a, 6b and 6c show the correction according to the invention in a three-dimensional representation.

DETAILED DESCRIPTION OF THE INVENTION

Figure 1:
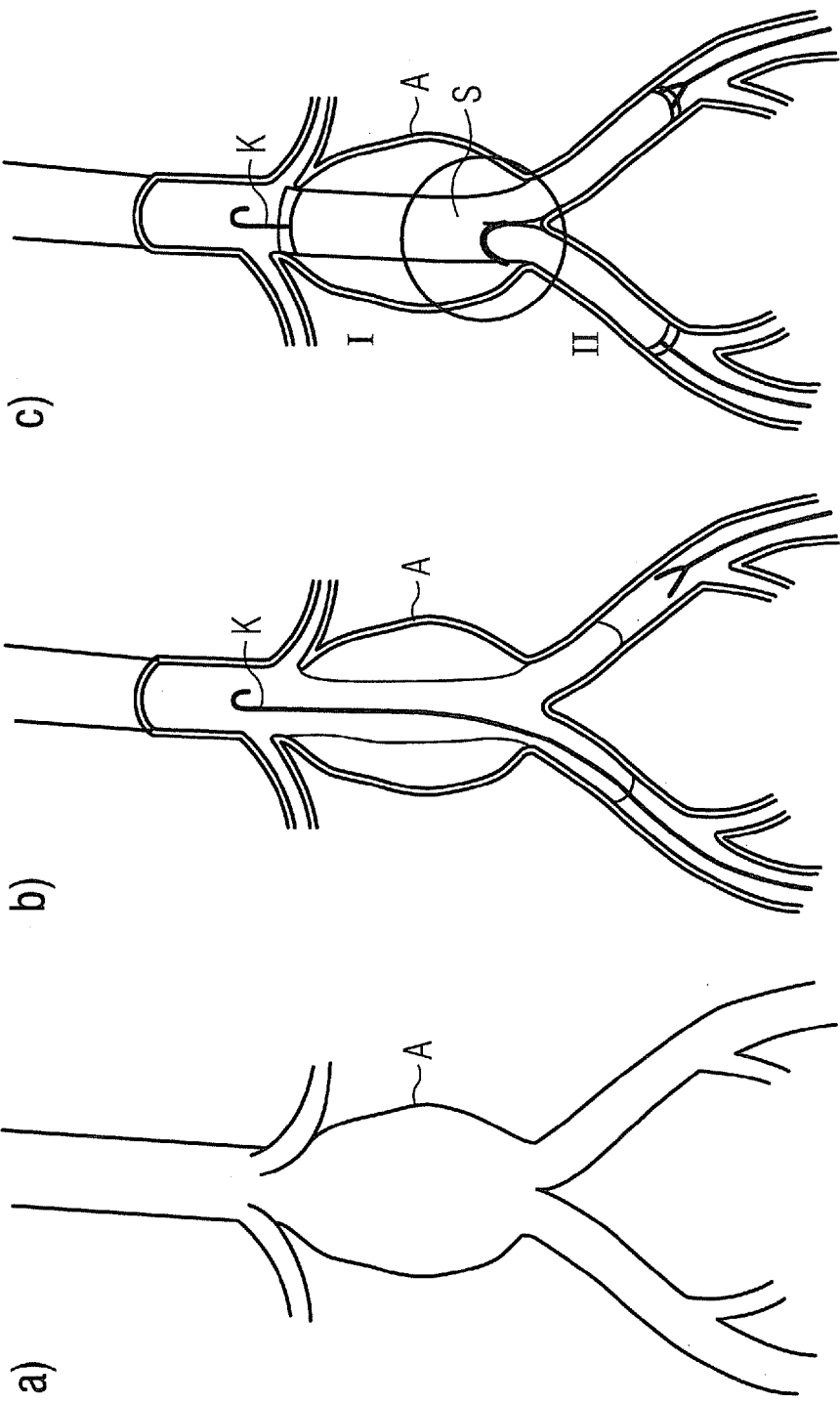
Figure 4:
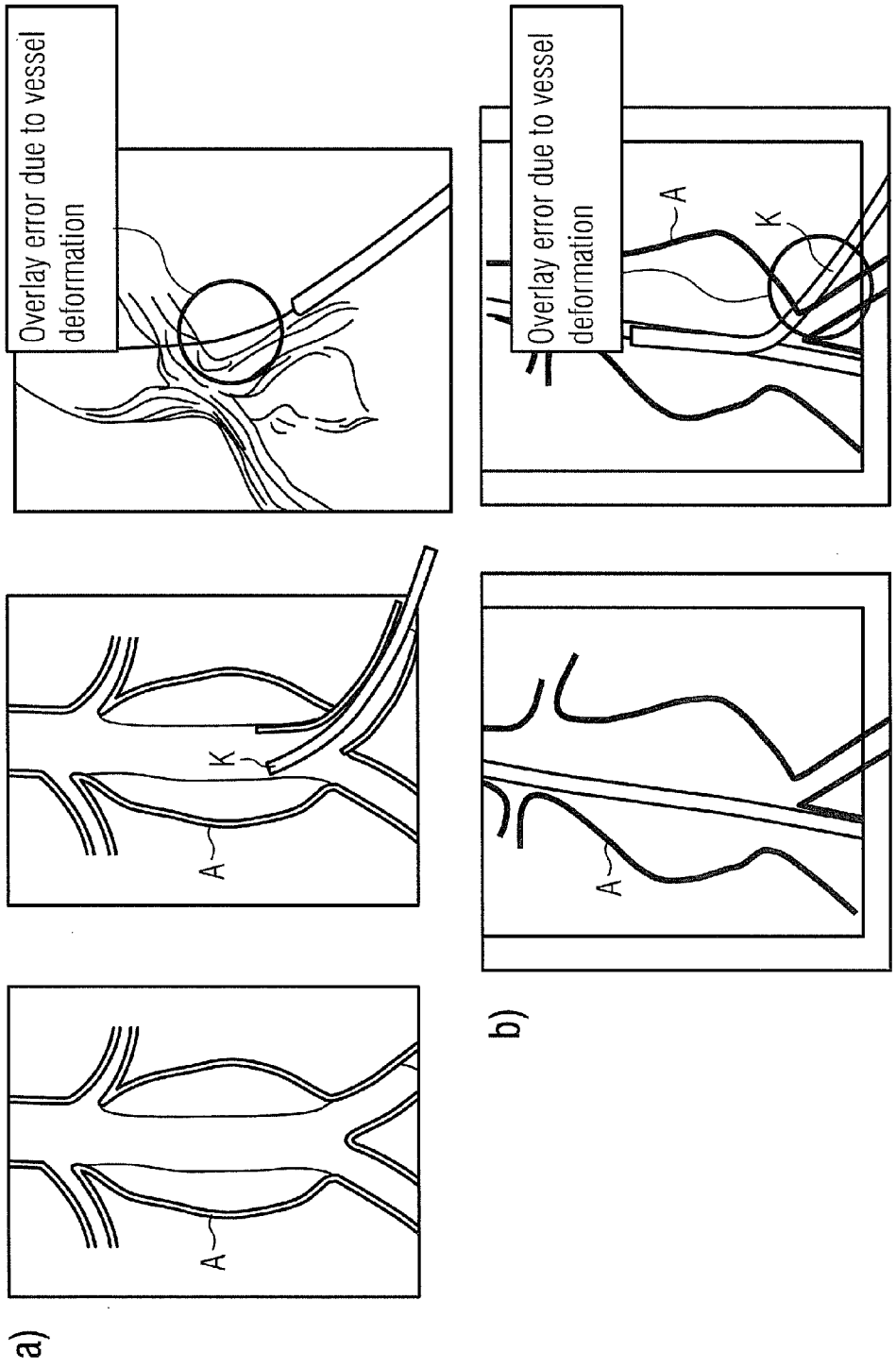

In the following the principle of the correction according to the invention is described with reference to the repair of an aortic aneurysm in the following embodiment variants:

Ideally the following preconditions are established:

1. A reference dataset, registered with respect to the C-arm (or, as the case may be, the respective fluoroscopic images), which represents either a 3D volume, e.g. a previously performed CT angiography, or a C-arm CT recorded during the intervention, or else 2D images, e.g. angiography sequences (DSA) of the corresponding vessels, 2. information relating to the course (e.g. the so-called centerline) of the vessels or the course of vessel contours and/or other corresponding information, as shown for example in FIG. 3, in the reference images, e.g. relating to a (semi-)automatic 2D or 3D segmentation (depending on dataset used), and 3. a means of detecting and tracking the instrument(s) introduced, e.g. the instrument for introducing the stent. This can happen e.g. by way of a corresponding identification or tracking of the instruments in the fluoroscopic images.

As shown in FIG. 5, the procedure according to the invention is preferably performed in the following sequence:

The position detected in the fluoroscopic image identifies the current course of the vessel, since the instrument is located inside the vessel.

The reference image (or the centerline of the segmentation of the reference image) is then adapted (updated) accordingly or, as the case may be, distorted or, as the case may be, displaced or, as the case may be, deformed so that the current vessel course and assumed vessel course are consistent once again. In this case the corresponding part of the vessel in the reference image is brought into congruence with the current vessel course resulting from the position of the detected instrument, e.g. a catheter K, as shown for example in FIG. 5a. The reference image is adapted differently according to position and penetration depth of the instrument; see e.g. also FIG. 5b.

The remainder of the vessel course (i.e. the part in which no instrument has yet been introduced) is extrapolated e.g. on the assumption of "smoothness conditions", i.e. generally the vessels have no abrupt bends or similar. In this case regions remote from the detected instrument are not deformed (e.g. the renal arteries when an instrument is introduced into the leg arteries) and closer regions are deformed in such a way that a smooth vessel course is preserved.

In the deformation of the reference image (in particular of a 3D vessel) attention can also be devoted in particular to a "trueness to length", since an introduced instrument does not change the length of the centerline of the vessel. By way of these boundary conditions it is possible in particular to correct deviations which initially are not visible in the image on account of the viewing angle, as shown for example in FIG. 6a. If the vessel is e.g. curved "in the viewing direction", i.e. perpendicular to the image plane, an introduced instrument initially creates no visible displacement between overlaid reference image and fluoroscopic image. However, if the curvature of the centerline is known by way of the segmentation, the stretching produced by the instrument can be computed and consequently e.g. the displacement of a branch vessel from its actual location computed, and the overlay can then be adapted accordingly, as shown for example in FIGS. 6b and 6c.

Optionally, the following embodiment variants are conceivable. The information relating to the course of the vessel (in 2D or in 3D)

can also be defined manually by the user (e.g. by means of a marker), can also be given by means of a mathematical description, e.g. a higher-order polynomial or another suitable function. The overlay can then be adapted e.g. by way of the updating of the function parameters according to the position of the detected instrument.

Optionally or alternatively, the position of the introduced instrument can be defined manually by the user, determined via a position-transmitting sensor, determined or reconstructed three-dimensionally with the aid of two or more X-ray images from a number of angles.

It is advantageous that not just one, but a plurality of instruments are detected or tracked. This enables e.g. other stationary instruments (e.g. guide wires introduced into the renal arteries) to be identified and tracked as well in order to ensure the consistency of the overlay at a plurality of points.

It is also conceivable for the method to be applied in other interventional procedures that benefit from the overlaying of preferably pre-segmented reference images. The replacement of aortic valves, interventions in coronary blood vessels, etc. are conceivable as other interventional procedures.

LIST OF REFERENCE SIGNS

A Abdominal aortic aneurysm
S Stent graft
K Catheter

The invention claimed is:

1. A method for adapting a reference image, comprising:
extracting an assumed course of the blood vessels from the reference image;
introducing an instrument into a target region which deforms the assumed course of the blood vessels;
detecting a position of the introduced instrument in a fluoroscopic image;
identifying a current vessel course based on the position of the introduced instrument in the fluoroscopic image;
registering and overlaying the reference image with the fluoroscopic image which comprises a deformation as a result of the introduced instrument;
correcting the deformation in the overlaid reference image based on the current vessel course so that the current vessel course and the assumed course of the blood vessels are consistent; and
extrapolating a part of the current vessel course in which the instrument has not been introduced in the overlaid reference image based on smoothness condition, wherein the smoothness condition comprises no abrupt bends on the blood vessels.

2. The method as claimed in claim 1, wherein the part of the current vessel course in which the instrument has not been introduced is not deformed in the overlaid reference image.

3. The method as claimed in claim 1, wherein the deformation which is hidden due to a viewing angle in the reference image is corrected.

4. The method as claimed in claim 1, wherein the current vessel course is determined manually.

5. The method as claimed in claim 1, wherein the current vessel course is described by a mathematical function.

6. The method as claimed in claim 5, wherein the mathematical function is a higher-order polynomial.

7. The method as claimed in claim 5, wherein parameters of the function are updated in accordance with the position of the introduced instrument.

8. The method as claimed in claim 1, wherein the position of the introduced instrument is defined manually by a user.

9. The method as claimed in claim 1, wherein the position of the introduced instrument is determined by a position-transmitting sensor.

10. The method as claimed in claim 1, wherein the position of the introduced instrument is determined or reconstructed from one or more fluoroscopic images.

11. The method as claimed in claim 1, wherein the fluoroscopic images are taken from a number of recording angles.

12. The method as claimed in claim 1, wherein the reference image is a previously recorded multidimensional image of the target region.

13. The method as claimed in claim 1, wherein an assumed blood vessel contour is extracted from the reference image.

\* \* \* \* \*